United States Patent
Pilly et al.

(10) Patent No.: US 11,237,634 B2
(45) Date of Patent: Feb. 1, 2022

(54) SYSTEM AND METHOD FOR ASYNCHRONOUS BRAIN CONTROL OF ONE OR MORE TASKS

(71) Applicant: HRL LABORATORIES, LLC, Malibu, CA (US)

(72) Inventors: Praveen Pilly, West Hills, CA (US); Jaehoon Choe, Agoura Hills, CA (US); Michael Howard, Westlake Village, CA (US); Nicholas Ketz, Madison, WI (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 17/112,052

(22) Filed: Dec. 4, 2020

(65) Prior Publication Data

US 2021/0240265 A1    Aug. 5, 2021

Related U.S. Application Data

(60) Provisional application No. 62/970,079, filed on Feb. 4, 2020.

(51) Int. Cl.
| | |
|---|---|
| *G06F 9/46* | (2006.01) |
| *G06F 3/01* | (2006.01) |
| *G06F 9/54* | (2006.01) |
| *G06F 9/48* | (2006.01) |
| *A61B 5/291* | (2021.01) |

(52) U.S. Cl.
CPC .............. *G06F 3/015* (2013.01); *A61B 5/291* (2021.01); *G06F 9/4843* (2013.01); *G06F 9/544* (2013.01)

(58) Field of Classification Search
CPC .............................. G06F 3/015; G06F 9/4843
See application file for complete search history.

(56) References Cited

U.S. PATENT DOCUMENTS

| | | |
|---|---|---|
| 2004/0097824 A1 | 5/2004 | Kageyama |
| 2008/0235164 A1* | 9/2008 | Tian ..................... G06F 3/0482 706/12 |

(Continued)

FOREIGN PATENT DOCUMENTS

KR    10-2015-0106954 A    9/2015

OTHER PUBLICATIONS

Jackson et al., "Core Algorithms of the Maui Scheduler," Springer-Verlag Berlin Heidelberg 2001, Brigham Young University, Provo, Utah 84602, pp. 87-102, 2001.

(Continued)

*Primary Examiner* — Camquy Truong
(74) *Attorney, Agent, or Firm* — Lewis Roca Rothgerber Christie, LLP

(57) ABSTRACT

A closed-loop system for asynchronous brain control of at least one task includes a brain state decoder configured to decode neural signals of a user into control signals for controlling the at least one task, a task interface module configured to transmit the control signals to the at least one task, store status information including a series of messages regarding each of the at least one task, and select one message of the series of messages regarding the at least one task to transmit to the user, and a brain state encoder configured to map the one message received from the task interface module into brain state montages for transmission to the user.

20 Claims, 7 Drawing Sheets

(56) References Cited

U.S. PATENT DOCUMENTS

| | | |
|---|---|---|
| 2010/0137734 A1 | 6/2010 | Digiovanna et al. |
| 2010/0293312 A1* | 11/2010 | Sonnier ................ H04L 49/506 |
| | | 710/107 |
| 2012/0245713 A1 | 9/2012 | Chen et al. |
| 2014/0277582 A1 | 9/2014 | Leuthardt et al. |

OTHER PUBLICATIONS

Spüler, "A high-speed brain-computer interface (BCI) using dry EEG electrodes," Plos One, 12 pages, 2017.
Stepp et al., "Relative to direct haptic feedback, remote vibrotactile feedback improves but slows object manipulation," 32nd Annual International Conference of the IEEE EMBS, 4 pages, 2010.
Tan et al. "Decoding gripping force based on local field potentials recorded from subthalamic nucleus in humans," eLIFE, 24 pages, 2016.
International Search Report and Written Opinion for Application No. PCT/US2020/063274, dated Mar. 15, 2021, 10 pages.

* cited by examiner

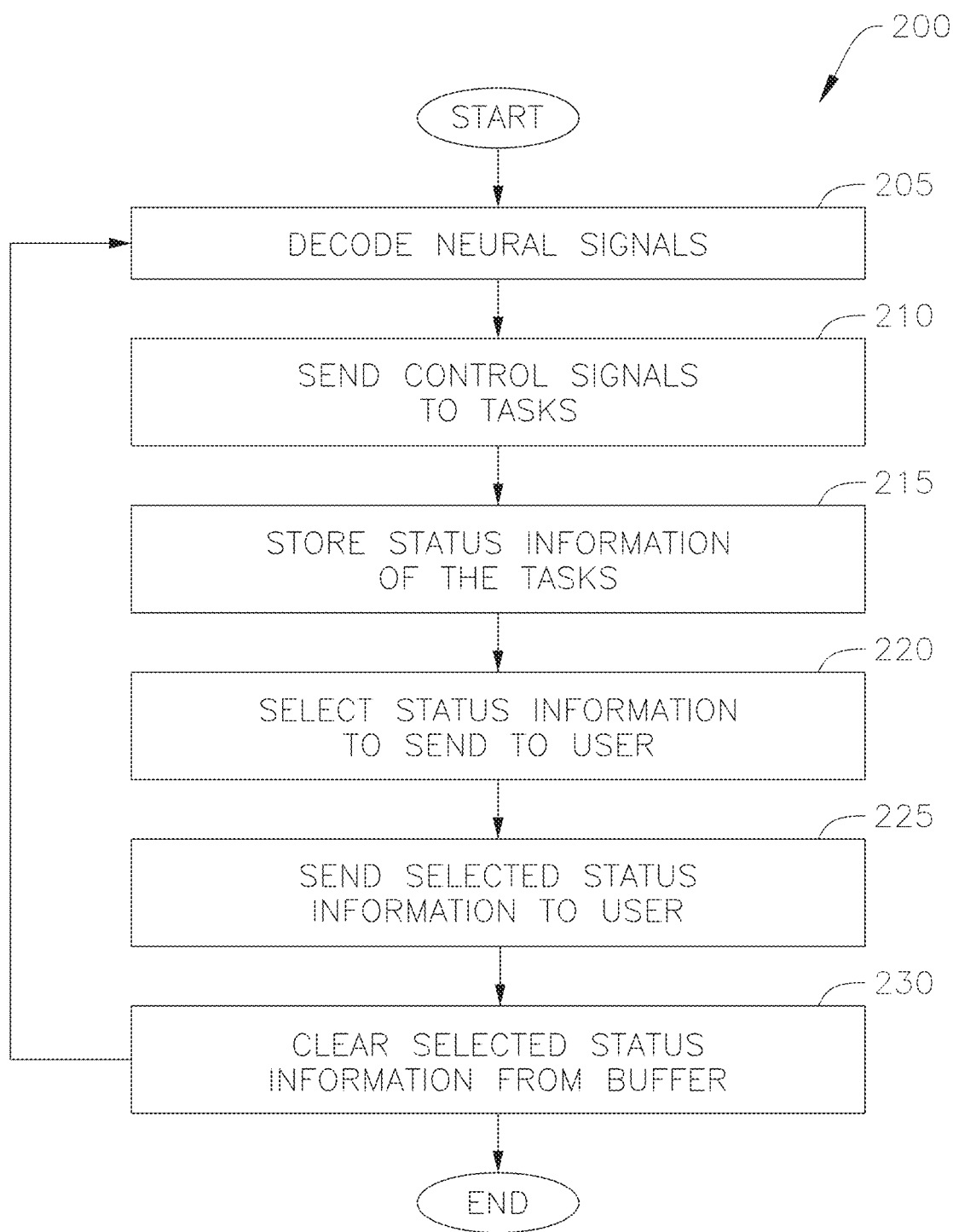

SYSTEM AND METHOD FOR ASYNCHRONOUS BRAIN CONTROL OF ONE OR MORE TASKS

CROSS-REFERENCE TO RELATED APPLICATION(S)

The present application claims priority to and the benefit of U.S. Provisional Application No. 62/970,079, filed Feb. 4, 2020 in the U.S. Patent and Trademark Office, the entire content of which is incorporated herein by reference.

BACKGROUND

1. Field

Embodiments of the present disclosure relate generally to systems and methods for asynchronous brain control of tasks.

2. Description of Related Art

A variety of brain-machine-interface (BMI) devices exist to enable a user to control a device based on the neural signals generated by a user. However, related art BMI devices including cognitive control are single-task systems (i.e., related art cognitive control-based BMI devices enable the user to control only a single task of a device). For instance, one related art method for controlling a docking maneuver of a satellite includes displaying a number of command icons on a display, each blinking at certain unique times, which caused a P300 electroencephalography (EEG) signal to be generated when the user viewed the blinking command icons. By comparing the timing of the P300 EEG signal to the time of the blink of each command icon, this related art system could deduce which command to execute on the satellite.

However, this related art system is relatively slow, taking on the order of seconds to perform the commands. Additionally, with this related art method, the user must foveate on a particular blinking display to send a control signal, thus losing awareness of the situation he/she is in. Finally, these methods do not provide a way for the user to ascertain the status of the controlled device in a non-sensory manner. Instead, the user must devote sensory resources to acquiring and maintaining awareness of the controlled device or task, reducing the sensory resources available for awareness of the user's surroundings and personal safety.

Furthermore, related art systems and methods for multitasking are slow because the user experiences a time lag in reacquiring situational awareness when switching between tasks. Cognitive situational awareness requires maintaining salient and relevant details in the brain's limited working memory area. When an individual changes tasks (e.g., from a foreground task to a background task), the details of the background task must be copied into working memory from a short-term memory store in the individual's hippocampus. The working memory representation must then be updated to reflect the current state of any dynamic aspects of the new foreground task. These processes of copying the short-term memory to working memory and updating the working memory are time-consuming, which makes related art methods of multitasking slow and inefficient.

SUMMARY

The present disclosure relates to various embodiments of a closed-loop system for asynchronous brain control of one or more tasks. In one embodiment, the system includes a brain state decoder configured to decode neural signals of a user into control signals for controlling the one or more tasks, a task interface module configured to transmit the highest priority control signals to the one or more tasks, store status information regarding each of the one or more tasks, and select the status information of one of the one or more tasks to transmit to the user, and a brain state encoder configured to map the status information received from the task interface module into brain state montages for transmission to the user.

The task interface module may include at least one status buffer configured to store the status information of the at least one task, and a status selector module programmed with an algorithm configured to select the status information of the one of the at least one task based on a classification of the status information, a recency parameter, and a priority of the at least one task.

The algorithm may include a weighting parameter R weighing on the recency parameter $\Delta t_{msg}$. The weighting parameter may be a constant value or a function of the recency parameter. The function may be a non-linear function.

The algorithm may be BufferPriorities=$P_{buffer}$*(max$_{msg_1}^{msg_n}$(UrgencyValue$_{msg}$*R*$\Delta t_{msg}$)), wherein msg$_1$ through msg$_n$ are the messages of the status information regarding the one or more tasks, n is a number of tasks (the number of tasks being one or more), $P_{buffer}$ is a priority of the task buffer(s) storing the messages (the message buffer uniquely allowed to contain messages related to a particular task) relative to the priorities of any other task buffers (where these priorities are assigned by the user who adds the task), UrgencyValue$_{msg}$, is an urgency value based on a classification of the status information (assigned by the user for each message type used in the task relative to every other message type used by the task), $\Delta t_{msg}$ is a recency parameter, and R is a weighting parameter reflecting the importance of the recency parameter. The value assigned to UrgencyValue$_{msg}$ for a particular type of message (msg) may be based on the likelihood of loss or damage if the message is ignored. For example, message types that convey critical failures in the controlled task (e.g., message type ERROR) might be assigned higher UrgencyValue than message types that convey benign status updates (e.g., message type INFORMATION or WARNING).

The task interface module may further include a command multiplexer configured to transmit the control signals to the one or more tasks.

The task interface module may further include a status multiplexer configured to transmit the status information of the one of the at least one task to the brain state encoder.

The one or more tasks may be performed on a same semi-autonomous device or on two or more separate semi-autonomous devices. For example, in one or more embodiments, a flying platform might have a task related to steering and navigation, and a different task related to controlling a video or audio sensor and analyzing the data in search of particular objects of interest.

The present disclosure also relates to various methods for asynchronous control of at least one task in a closed-loop system. In one embodiment, the method includes decoding, with a brain state decoder, neural signals of a user into a command signal, transmitting the command signal to the at least one task, storing, in status buffers, status information including a series of messages regarding the at least one task, selecting, with a status selector module programmed with an algorithm, one message of the series of messages, and encoding, with a brain state encoder, the one message regarding the at least one task into state brain state montages for transmission to the user.

The method may include obtaining the neural signals invasively or non-invasively from the user.

The method may also include transmitting the brain state montages directly to the user's short-term memory, and the brain state montages may be configured to create a non-sensory cognitive perception in the user of the status information regarding the second task.

The algorithm may include a classification of the messages, a recency parameter, and a priority of the messages.

The algorithm may include a weighting parameter weighing on the recency parameter. The weighting parameter may be a constant value or a function of the recency parameter. The function may be a non-linear function.

The algorithm may be BufferPriorities=$P_{buffer}$*(max$_{msg_1}^{msg_n}$(UrgencyValue$_{msg}$*R*$\Delta t_{msg}$)), wherein msg$_1$ through msg$_n$ are the messages of the status information regarding the one or more tasks, n is a number of tasks (the number of tasks being one or more), $P_{buffer}$ is a priority of the task buffer(s) storing the messages (the message buffer uniquely allowed to contain messages related to a particular task) relative to the priorities of any other task buffers (where these priorities are assigned by the user who adds the task), UrgencyValue$_{msg}$, is an urgency value based on a classification of the status information (assigned by the user for each message type used in the task relative to every other message type used by the task), $\Delta t_{msg}$ is a recency parameter, and R is a weighting parameter reflecting the importance of the recency parameter.

The present disclosure also relates to various embodiments of a closed-loop system for asynchronous brain control of at least one task. In one embodiment, the system includes means for decoding neural signals of a user into a command signal, means for transmitting the command signal to the at least one task, means for storing status information including a series of messages regarding each of the at least one task, means for selecting one message from the series of messages regarding the at least one task, and means for encoding the one message regarding the at least one task into brain state montages for transmission to the user.

This summary is provided to introduce a selection of concepts that are further described below in the detailed description. This summary is not intended to identify key or essential features of the claimed subject matter, nor is it intended to be used in limiting the scope of the claimed subject matter. One or more of the described features and/or tasks may be combined with one or more other described features and/or tasks to provide a workable device and/or a workable method.

BRIEF DESCRIPTION OF THE DRAWINGS

These and other features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale.

FIG. 4 is a flowchart illustrating tasks of a method of asynchronous brain control of two or more tasks according to an embodiment of the present disclosure;

DETAILED DESCRIPTION

Figure 1:
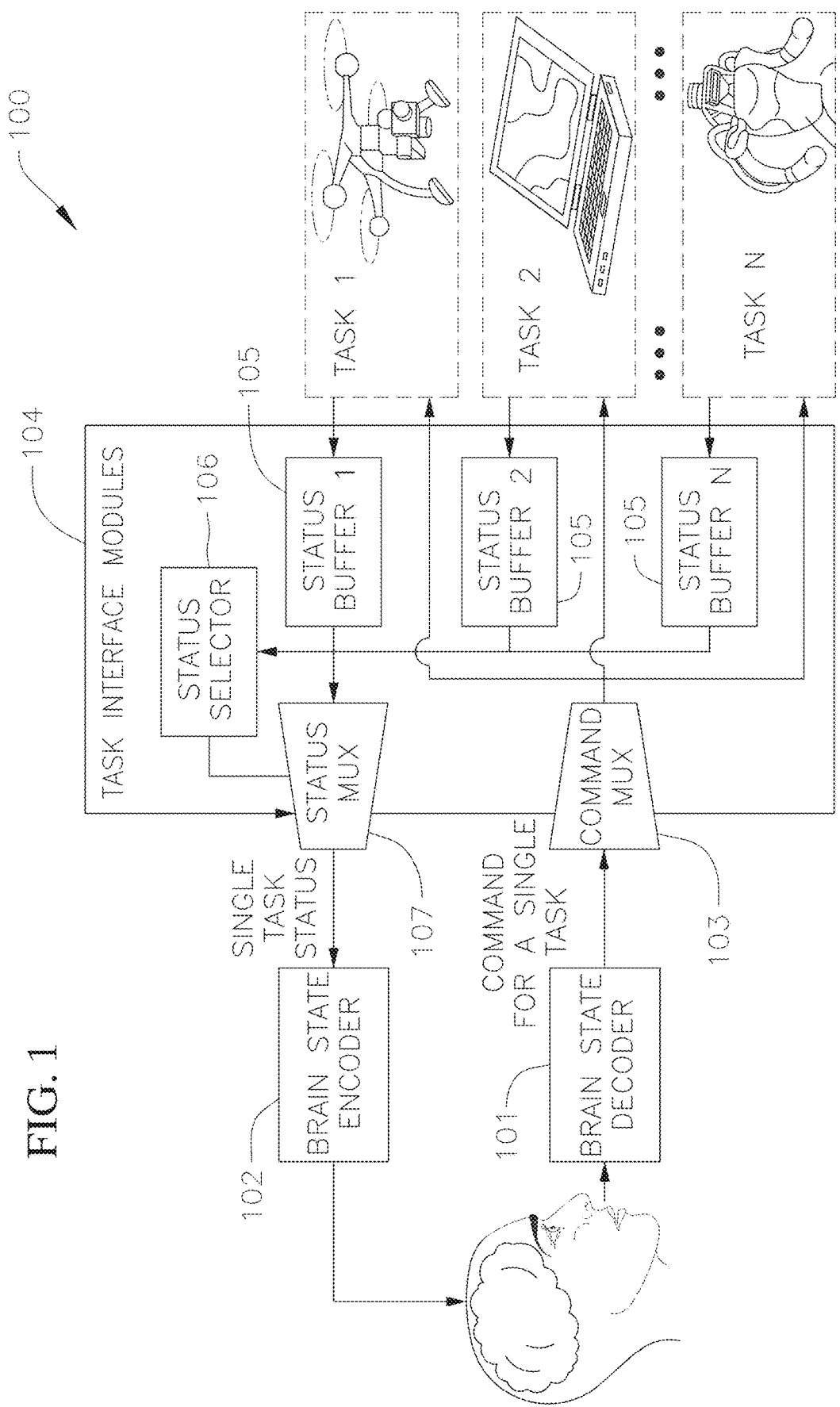
FIG. 1 is a schematic block diagram of a system configured to enable asynchronous brain control of one or more tasks according to an embodiment of the present disclosure.

The present disclosure relates to various embodiments of systems and methods for enabling asynchronous cognitive control of two or more tasks utilizing application-agnostic bi-directional human-machine communication. Embodiments of the systems and methods of the present disclosure are configured to reduce the amount of time it takes for the user to reacquire cognitive situational awareness when switching between the tasks by utilizing a direct neural interface that can be serviced and processed independently of the user's senses (i.e., signals or data are transmitted or communicated to the user's nervous system in a manner that bypasses the user's physical senses). Reducing the amount of time it takes the user to reacquire cognitive situational awareness enables the user to rapidly switch between performing the two or more tasks. For instance, while the user is involved with the performance of a first task (Task A), data (e.g., status information) regarding a second task (Task B) can bypass the user's senses and be transmitted directly to the user's short-term memory utilizing embodiments of the systems and methods of the present disclosure. Keeping the user informed in this manner of the status of Task B while performing Task A minimizes or at least reduces the lag time for the user to reacquire situational awareness of Task B, which enables the user to quickly regain effective, informed control of Task B after switching away from performing Task A.

In one or more embodiments, the systems and methods of the present disclosure utilize a brain state encoder with a direct neural interface to enable data obtained from a secondary task to bypass the user's senses and to be fed directly into the user's short-term memory while the user is performing a primary task. Additionally, in one or more embodiments, the systems and methods of the present disclosure utilize a brain state decoder to output control signals for two or more tasks based on the user's brain state (e.g., dynamic properties of the brain, such as blood flow and/or electrical emanations). In this manner, embodiments of the systems and methods of the present disclosure enable a user to supervise and control multiple tasks asynchronously by switching rapidly between the tasks because the direct neural interface reduces the user's time lag in reacquiring situational awareness of the secondary task after switching away from performing the primary task. That is, embodiments of the systems and methods of the present disclosure enable cognitive control of multiple tasks and avoid or at least reduce the related art situational awareness acquisition penalty because cognitive awareness is constantly updated directly in the user's working memory in a direct, non-sensory manner. The systems and methods of the present disclosure may be utilized to enable asynchronous, low-latency cognitive control of any semi-autonomous device capable of accepting discrete commands, such as, for instance, air vehicles (e.g., UAVs), ground vehicles, water vehicles, humanoid robots (e.g., a robot arm), or interfaces of computers. As used herein, the term "discrete commands" refers to a command that is individually separate and distinct (i.e., not continuous). As an example, the user might be trained to visualize a movement vector as an egocentric arrow. The brain decoder can be trained to recognize such a brain state, and encode a command message for the task. Additionally, in one or more embodiments, the systems and methods of the present disclosure are configured to enable continuous, asynchronous cognitive control of the one or more tasks for a sustained duration, such as, for example, 1 minute, or 5 minutes, or 30 minutes, or 2 hours, or so on, limited only by the user's need to rest or sleep and the brain encode/decode system's ability to continue to interface with the brain. Continuous control is implemented by a stream of discrete commands to a task, and discrete feedback from the task.

With reference now to FIG. 1, a closed-loop system 100 for enabling asynchronous control of one or more tasks includes a brain state decoder 101 configured to receive dynamic properties of a user's brain (e.g., blood flow properties and/or electrical emanations that are indicative of neural signals) and to decode these dynamic properties of the user's brain into output control signals to control the one or more task. In the illustrated embodiment, the system 100 also includes a brain state encoder 102 configured to receive status information (e.g., data) from the one or more task and to encode this status information into transcranial stimulation patterns (e.g., brain stimulation montages) which, when transmitted to the user, invoke a brain state that causes a non-sensory cognitive perception of the status of the tasks being performed by the user utilizing the system 100. In one or more embodiments, the brain state encoder 102 is configured to supply the status information as non-sensory neural information to the user. The one or more tasks may be one or more tasks performed on the same semi-autonomous device or on two or more separate semi-autonomous devices, such as, for instance, air vehicles (e.g., a UAV), ground vehicles, water vehicles, humanoid robots, or interfaces of computers (e.g., desktop or laptop computers). In one or more embodiments, the brain state decoder 101 and the brain state encoder 102 may have any suitable type or kind of direct neural link to the user. For instance, in one or more embodiments, the brain state decoder and the brain state encoder may be configured to sense the user's neural signals and transmit neural signals to the user, respectively, either invasively (e.g., from sensors surgically implanted inside the brain) or non-invasively (e.g., by sensors placed outside the user's skull). The brain state decoder 101 and the brain state encoder 102 may be any type or kind of decoder and encoder, respectively, suitable for the types of tasks the system 100 is designed to control and depending, for instance, on the desired accuracy and latency of the system 100. In one or more embodiments, the brain state decoder 101 may be the brain-machine interface decoder disclosed in U.S. patent application Ser. No. 16/890,406, filed Jun. 2, 2020, and entitled "System and Method for Continual Decoding of Brain States to Multi-Degree-of-Freedom Control Signals in Hands Free Devices," that is configured to learn a transformation between a specific user's neural data while the user is visualizing the desired control of a task, the entire content of which is incorporated herein by reference.

Figure 5:
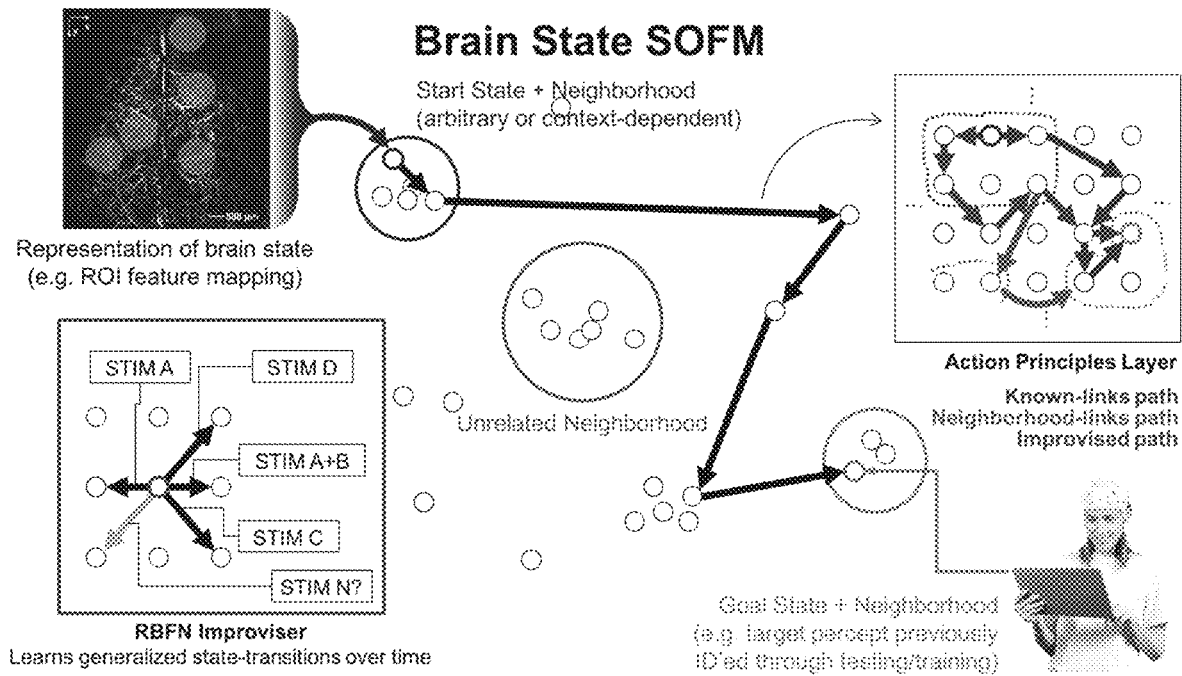
FIG. 5 is a brain state self-organizing feature map (SOFM) according to one embodiment of the present disclosure.

The brain state encoder 102 may be any suitable type or kind of brain state encoder. FIG. 5 depicts a brain-state (BS) self-organizing feature map (SOFM). The encoding system is personalized based on brain state representations derived from fused sensor signals acquired during testing and training sessions. In FIG. 5, sub-regional activity bounded by Region of Interest coordinates represent brain states. These states are then mapped into a Self-Organizing Feature Map (SOFM), which clusters brain states containing similar features. In this example depicted in FIG. 5, the goal state is a state-node associated with a desired percept identified in the training phase. In order to transition from the initial state to the goal state, stimulation interventions are represented as action principles between brain state SOFM nodes. Each link consists of a representation of the stimulation (e.g., volumetric electric fields) associated with a state-action-state triad. The action-principle layer (APL) consists of known (observed) transitions between state-nodes and node-clusters; transitioning from start state to goal state in these cases can be achieved simply by path planning backwards from the goal. If no known paths exist, a radial basis function network (inset, left) is used to learn general rules about directionality within action-link space to bridge the nodes.

Figure 6:
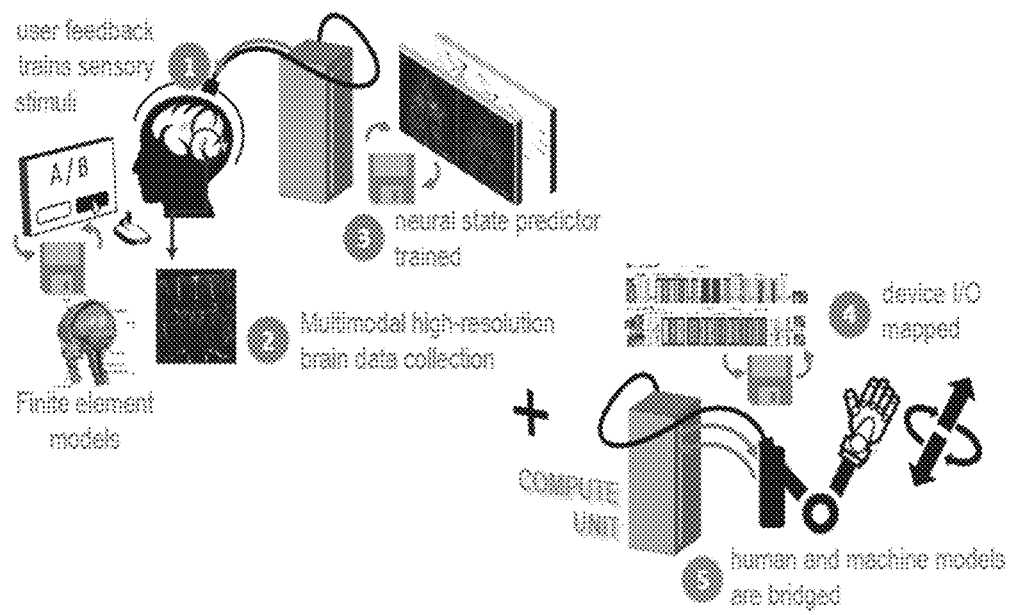
FIG. 6 is a schematic block diagram depicting pre-training of the system.

A Self-Organizing Feature Map (SOFM) is a type of artificial neural network that is trained using unsupervised learning to produce a low-dimensional (e.g., two-dimensional), discretized representation of the input space of the training samples, called a map, and is therefore a method to do dimensionality reduction, and clustering. The task is to read the brain activity data, cluster it into the most similar cognitive state, and then to provide transcranial stimulation to change that cognitive state into one which causes the user to perceive the sensory feedback. The lower layer of the BS-SOFM represents what is called the Action Principles Layer in FIG. 5. This is a self-organized feature map of percept-action-percept triads that links action principles (stimulation parameters) to brain states for seamless activation of specific percepts in the user's brain that are robust to context (the user's initial brain state), and are sensitive to the sequential aspects of both perceptual and action representations. The method includes iteratively applying stimulus patterns so as to drive or steer the brain's cognitive state into the desired state. A pre-training phase is used to capture information to train the SOFM concerning the application control space as well as consideration of the input signal type and environmental noise that will be present during use (see FIG. 6). During pre-training, finite element models are derived from structural imaging data (FIG. 6, step 1). The user will perform a series of tasks in the context of interest with varying cognitive loads. In particular, while the user explores the degrees of freedom for various tasks, multimodal high-resolution brain activity data is acquired (FIG. 6, step 2) to learn the initial predictive relationships between the fused brain data and the control signals in the brain state decoder module (FIG. 6, step 3). Brain activity data is also acquired while the subject is perceiving or visualizing each of the categories of sensory feedback from the device sensors about the task environment, to be stored as potential goal states in the SOFM lookup table. This data is used to identify regions of the brain with the most informative activations as control signals (clustered into nodes in the cognitive states network of the SOFM), and for calculating subject-specific transforms (for the action-principles layer) to align these regions across users (FIG. 6, step 4). Separately, calibration data is obtained by recording brain state dynamics as high-definition transcranial current stimulation (HD-tCS) pulses of varied montages and parameters are applied to initially train the encoder module to be able to rapidly compute a trajectory in HD-tCS space for steering brain activity from an arbitrary start state to a desired goal state (FIG. 6, step 5).

A cap/helmet equipped for recording brain signals is fitted to the user in order to begin training the system algorithms governing the learning of neural patterns for feedback. This allows for learning a personalizable policy of neurostimulation mapped to subjective experience. Depending on the brain stimulation technology, structural models are also developed based on vascular patterns and brain topology for the purpose of generating finite-elements modeling (FEM) predictions of current spread throughout the brain and refining beam-steering properties of electrical stimulation. HD-tCS includes these structural models for the most accurate stimulation.

The user is administered spatio-temporally varying signals targeting, for example, the somatosensory cortex and is asked to report subjective perceptions to map stimulation patterns to behavioral ends. The desired behavioral end of the inventive system is being able to convey to the user a certain sensory perception relative to the chosen task/context of interest, solely as a result of changing the user's brain state. That is, the user is unable to perceive the feedback using the 5 senses, but can perceive it due to the stimulation's effect on brain state. Also included within this human-in-the-loop testing are subjective measures of discernibility, in order to ensure that mapped sensory stimulation parameters induce sensory information that is clearly distinguishable across 6 or more categories (i.e., 6 or more distinct sensory feedback types). Categories can correspond to different distinct types of status information from the tasks, including any "information", "warning", or "error". Fused blood flow imaging (BOLD) and electrophysiology (EEG) is then computed in order to train the SOFM.

FEM models are generated and potential montages and protocols are computed using structural imagery of the user's brain. A dictionary of possible stimulation combinations and beam-steering properties are encoded and stored. The dictionary of neurostimulation intervention definitions are mapped to the neurophysiological/subjective sensory information to enable conversion from sensor percept to subjective sensory experience.

Action Principles (here, stimulation patterns/montages/protocol) are associated with subjective sensory states such that given a start sensory state, executing an Action Principle (AP) results in a predictable second sensory state. Using the dictionary of possible sensory states and stimulation patterns, we can then expand the vocabulary of Sensory State 4 AP 4 Sensory State such that solution paths over the graph can be created traversing a arbitrary start sensory state to a desired goal state through the execution of a precise sequence of AP. The vocabulary for the State-AP triad is automatically generated using a hybrid network leveraging self-organizing feature maps (SOFM).

The combination of the technologies used in the overall Brain-Computer Interface (BCI) system overcomes the primary obstacles for a robust, accurate, and non-invasive BCI and can operate agnostically across a wide range of signals data. As all of the resource-heavy computational steps have been completed in the prior tasks/processes, the only source of latency in the overall system is transmission delays existing between devices. This enables the use of the BCI in a variety of wide-ranging applications, including the control of hardware such as neuroprosthetics, drones, and even large groups of drones (swarms) with full bidirectional feedback and control.

During operation, when a sensory feedback state is available to deliver to the user, the user's cognitive state is sensed and matched with the states in the Brain State SOFM. Even if there is not a perfect match, the map will return the closest match, which is the current state. The sensory feedback state is the goal state, which is found using a lookup table of brain states (created above) that match sensory feedback states for the particular task/context of interest. The SOFM's Action-Principles Layer is used to search for a stimulus pattern that can be applied that will take the user's cognitive state closer to the desired state (found above). After each pattern is applied, the brain state is again sensed and the SOFM consulted for the next stimulus pattern to apply. These cycles can take place very rapidly on the order of 10's of milliseconds. When the goal state is reached (or a state that is clustered with the goal state) the sensory feedback has been delivered to the user.

Figure 7:
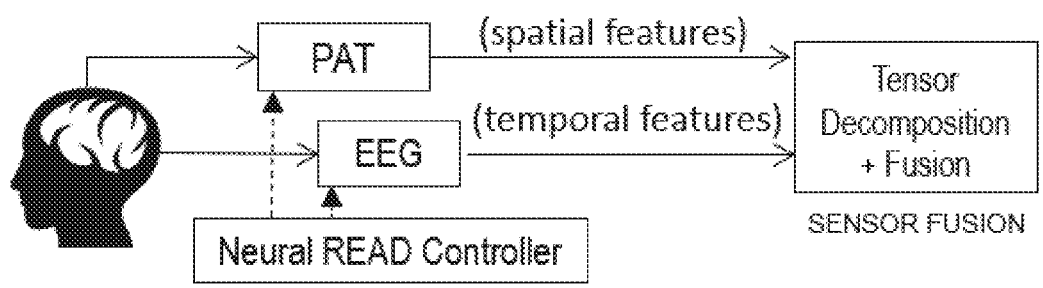
FIG. 7 is a schematic block diagram of a brain state encoder according to one embodiment of the present disclosure.

FIG. 7 depicts an implementation for sensing a brain state at high temporal and spatial resolution. In the illustrated embodiment, the system or device includes a PhotoAcoustic Tomography (PAT) device or technique and an electroencephalogram (EEG) device or technique. In the illustrated embodiment, PAT and EEG may be combined utilizing a tensor decomposition technique to fuse the multi-dimensional data in a way that employs the advantages of both technique (e.g., the brain state encoder 102 may utilize a method for sensor data fusion employing independent component analysis of tensors). PAT is a very high resolution sensing technique that can penetrate the human skull to provide a high-resolution image with only one-way distoration of ultrasound (compared to round-trip distorations of functional ultrasound), and it is complementary to EEG because of its low speed. PAT directly detecs both oxy- and deoxy-hemodynamic changes related to neural activities, and when fused with EEG will preserve high frequency features within high spatiotemporal brain imaging at less than or equal to approximately (about) 1 mm$^3$ spatial resolution and less than or equal to approximately (about) 10 millisecond (ms) temporal resolution. In one or more embodiments, the brain state encoder 102 may learn a self-organizing map that describe parameters for a combined PhotoAcoustic Tomography (PAT)/electroencephalogram (EEG), which will change any brain state into a state in which the user has a non-sensory experience of a particular situational awareness.

Accordingly, in one or more embodiments, the brain state encoder 102 is a method of producing cognitive states in a user that cause the user to experience a certain sensory perception, without involving the 5 senses. In one or more embodiments, the method includes a task of (a) a pre-training phase trains a Brain State Self-Organizing Feature Map (SOFM) to identify the brain regions whose activity correlates with the task and context of interest, and clusters their activity. As the user explored the degrees of freedom of the task/context of interest, each sensory feedback and the brain state it evokes is recorded in a lookup table; (b) an action-principles layer is trained by having the user exercise the degrees of freedom of the task/context of interest. It learns how each cognitive state will change when a certain stimulus pattern is applied and translates events in the world into temporal brain stimulation montages to apply non-invasively to a human brain in order to induce a perception of the event; and (c) during operation, each sensory feedback from the monitored system is converted into a goal cognitive state by consulting a lookup table. Current brain state is sensed, and a stimulation pattern chosen from the Action Principles Layer that will steer the user's current brain state closer to the goal state. This happens iteratively until the user's cognitive state is clustered with the goal state.

With continued reference to the embodiment illustrated in FIG. 1, the system 100 also includes a command multiplexer (MUX) 103 in one or more task interface modules 104 that is configured to receive the output signal from the brain state decoder 101 and configured to output command or control signals to the designated task (e.g., the designated device among two or more devices, or the designated task for a single device among two or more potential tasks for that single device). In one or more embodiments, the command MUX 103 may be configured to transmit the commands over any transmission medium suitable for the respective task (e.g., the command MUX 103 may be configured to transmit the commands for the tasks over a wired medium or a wireless medium).

In the illustrated embodiment, the system 100 also includes a series of status buffers 105 in the one or more task interface modules 104 that are configured to store status information (e.g., status updates) of the respective tasks. In the illustrated embodiment, the number of status buffers 105 is equal to the number of tasks (e.g., the number of tasks for a single device or the number of different devices) controlled by the system 100, and each status buffer 105 is configured to store the status information (e.g., the status updates) of only a single task. In the illustrated embodiment, the system 100 includes N status buffers 105 corresponding to N number of tasks the system 100 is configured to perform. In one or more embodiments, the brain state decoder 101 may be configured to decode the user's neural signals (e.g., as the user visualizes 6 degree of freedom motion from an egocentric perspective, where the degrees of freedom correspond to the 3 components of translation and 3 components of rotation) into a single 6 degree of freedom control command message for the movement task that controls a device (e.g., an aerial vehicle, a robot, a land vehicle, or a maritime vessel), and the task interface module 104 may include a task buffer 105 configured to store this movement command message such that the system 100 is configured to control each of the 6 degrees of freedom of the device. In one or more embodiments, storing the status information in individual status buffers 105 facilitates receiving status information asynchronously from the tasks.

In the illustrated embodiment, the one or more task interface modules 104 includes a status selector module 106 electrically connected to the status buffers 105. The status selector module 106 is configured to select which status information (i.e., the status information from which of the status buffers 105) to send to the brain state encoder 102 via a status multiplexer (MUX) 107. In one or more embodiments, the status selector module 106 is configured with a default task priority for each task, rules for evaluating individual status messages from the tasks, and a timing mechanism to ensure that each task gets to deliver status updates to the user via the brain state encoder at at least a minimum timing frequency, as described in more detail below.

Figure 2:
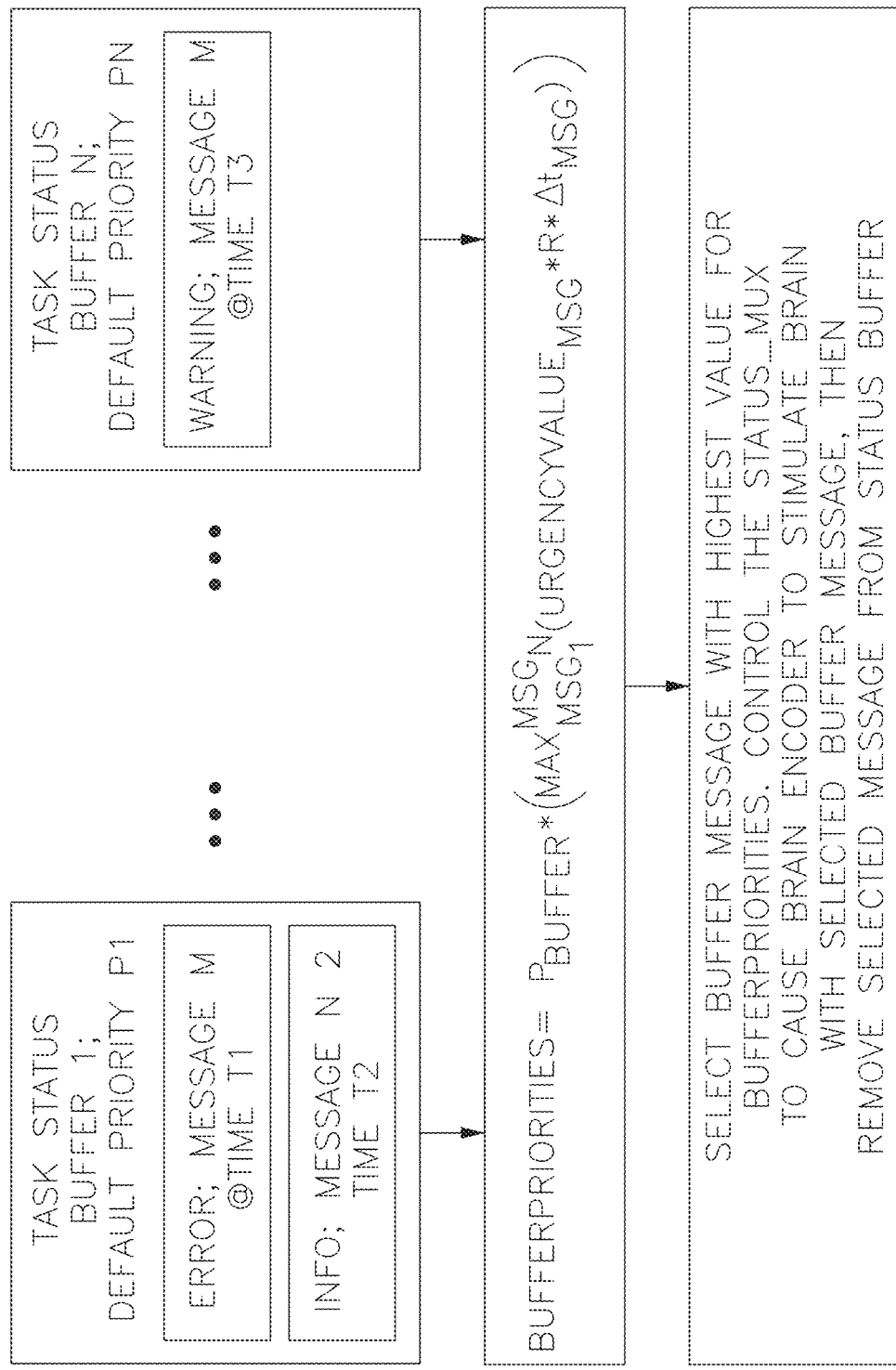
FIG. 2 is a schematic diagram of a status selector algorithm of the system of FIG. 1, according to an embodiment of the present disclosure.

FIG. 2 is a schematic block diagram illustrating the algorithm programmed on the status selector module 106 according to one embodiment of the present disclosure (e.g., FIG. 2 illustrates pseudo-code for controlling the operation of the status selector module 106 according to one embodiment of the present disclosure). In the illustrated embodiment, the algorithm of the status selector module 106 is configured to select the status information from one of the status buffers 105 that has the highest BufferPriorities value according to the following equation and send that status information to the user via the status MUX 107 and the brain state encoder 102:

$$\text{BufferPriorities(buffer)} = P_{buffer} * (\max_{msg_1}^{msg_n} (\text{UrgencyValue}_{msg} * R * \Delta t_{msg})) \quad \text{(Equation 1)}$$

In the illustrated embodiment, the algorithm of the status selector module 106 includes a priority parameter, $P_{buffer}$, for each of the tasks (e.g., primary priority for the task of controlling an autonomous aerial vehicle, secondary priority for the task of controlling an interface of a computer monitor, and tertiary priority for the task of controlling a humanoid robot). As used herein, the terms "tasks" and "buffers" are used synonymously or interchangeably because, in one or more embodiments, there is one message buffer representing each task. In one or more embodiments, the task priority may be input a-priori by the user. In the illustrated embodiment, the task priority multiplies the maximum urgency metric, $\text{UrgencyValue}_{msg} * R * \Delta t_{msg}$, of each task status message (i.e., $msg_1$ through $msg_n$) stored in the status buffer 105. Accordingly, the message to be selected for sending is the one with the maximum urgency metric in the buffer with the highest BufferPriority.

Additionally, in the illustrated embodiment, the algorithm of the status selector module 106 multiplies an urgency value, $\text{UrgencyValue}_{msg}$, based on the classification of the status information from the tasks. The value assigned to $\text{UrgencyValue}_{msg}$ for a particular type of message (msg) may be based on the likelihood of loss or damage if the message is ignored. For example, message types that convey critical failures in the controlled task (e.g., message type ERROR) might be assigned higher $\text{UrgencyValue}_{msg}$ than message types that convey benign status updates (e.g., message type INFORMATION or WARNING). In one or more embodiments, the urgency value, $\text{UrgencyValue}_{msg}$, may be set to one of three different values depending on whether the status information from the task is classified as "information," a "warning," or an "error." For instance, the urgency value, $\text{UrgencyValue}_{msg}$, may be set to the highest possible value when the status information from the respective task is classified as an error message, the urgency value, $\text{UrgencyValue}_{msg}$, may be set to the lowest possible value when the status information from the respective task is classified as information, and the urgency value, $\text{UrgencyValue}_{msg}$, may be set to an intermediate value when the status information from the respective task is classified as a warning (e.g., an error message may be assigned an urgency value, $\text{UrgencyValue}_{msg}$, of 3, a warning may be assigned an urgency value, $\text{UrgencyValue}_{msg}$, of 2, and information may be assigned an urgency value, $\text{UrgencyValue}_{msg}$, of 1). That is, in the illustrated embodiment, the algorithm of the status selector module 106 is configured to ensure that error messages get the highest priority for being transmitted to the user via the status multiplexer 107 and the brain state encoder 102, information gets the lowest priority, and warnings get an intermediate level of priority that is lower than the highest priority assigned to error messages and is higher than the lowest priority assigned to information. Although in the illustrated embodiment the algorithm of the status selector module 106 includes three different potential urgency values UrgencyValue$_{msg}$, in one or more embodiments, the algorithm of the status selector module 106 may include any other suitable number of different potential urgency values (e.g., more or less than three values) depending on the number of different classifications of the status information from the tasks. Additionally, in one or more embodiments, different values for the urgency value UrgencyValue$_{msg}$ may not increase linearly (e.g., the urgency values may increase exponentially).

In the illustrated embodiment, the algorithm for controlling the operation of the status selector module 106 also includes a recency parameter, $\Delta t_{msg}$, which denotes the amount of time that has elapsed since the message (msg) containing status information was stored in the status buffer 105. Additionally, in the illustrated embodiment, the algorithm for controlling the operation of the status selector module 106 includes a weighting parameter R configured to weigh the recency parameter, $\Delta t_{msg}$ (e.g., the weighting parameter R is configured to bias the importance of the recency parameter, $\Delta t_{msg}$). In one or more embodiments, the weighting parameter R may be input a-priori by the user. In one or more embodiments, the weighting parameter R may be set to a constant value (e.g., 1) or the weighting parameter R may be a function of the recency parameter, $\Delta t_{msg}$. For instance, in one or more embodiments, the weighting parameter R may be set as a non-linear function (e.g., an exponential function) of the recency parameter, $\Delta t_{msg}$, such that the priority of the status information would increase exponentially with the passage of time after the status information was stored in one of the status buffers 105. In one or more embodiments, the weighting parameter R may be a hard-coded time limit (e.g., the weighting parameter R may increase or be set to a predetermined value upon the recency parameter $\Delta t_{msg}$ reaching a preset time limit) or the weighting parameter R may be a function of a task-related variable. For instance, in one or more embodiments, the weighting parameter R may be a function of the speed of an autonomous vehicle controlled by the system 100 such that the weighting parameter R increases as the speed of the autonomous vehicle (and therefore the frequency at which status information changes) increases. In this manner, the weighting parameter R may be configured to increase the priority of sending the status information to the user via the status MUX 107 and the brain state encoder 102 as the frequency at which the status information from the task changes increases.

In the illustrated embodiment, the status selector module 106 is configured to select the status information message with the highest urgency metric from the buffer with the highest value for BufferPriorities (see Equation 1 above) and send this status information to the user via the status MUX 107 and the brain state encoder 102. Additionally, in one or more embodiments, the system 100 is configured to clear the status information stored in the status buffer 105 after that status information is sent to the user via the status MUX 107 and the brain state encoder 102. The algorithm of the status selector module 106 (e.g., the algorithm depicted in FIG. 2) is then repeatedly performed to determine the subsequent status information to send to the user via the status MUX 107 and the brain state encoder 102.

Figure 3A:
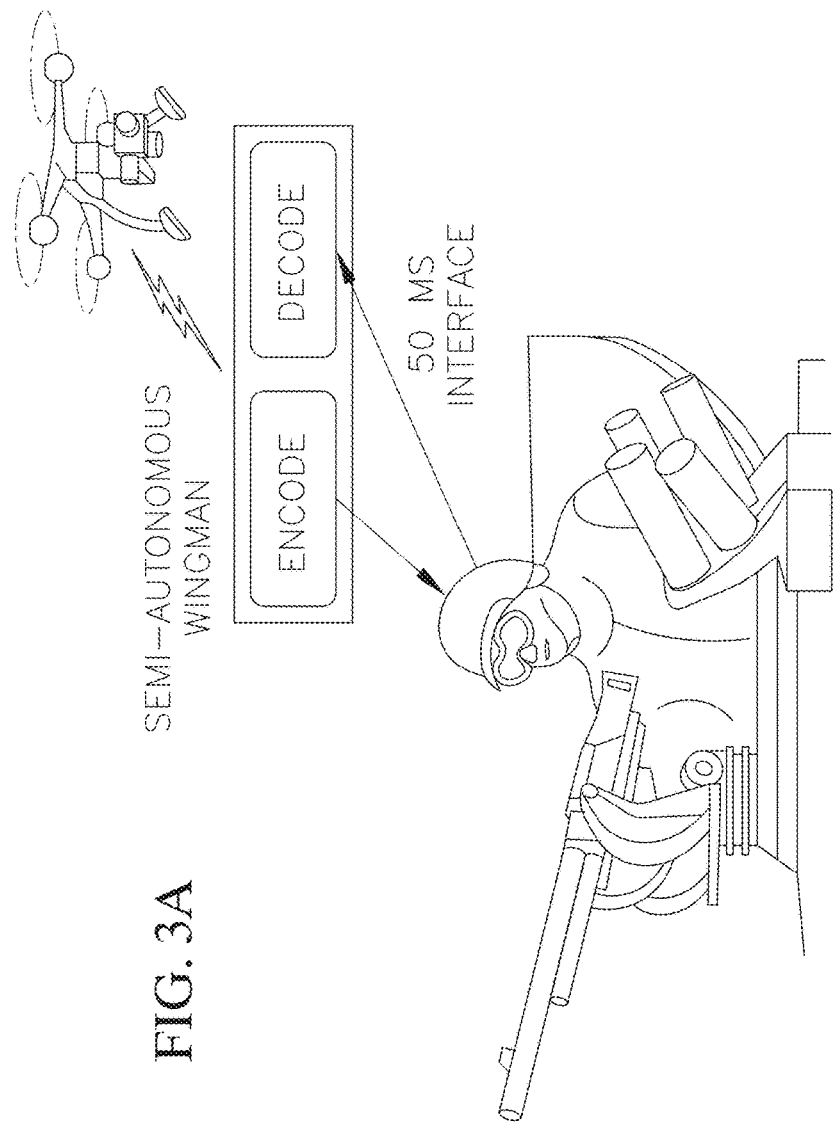
FIG. 3A is a perspective view of a user perform a primary task (gunner) and utilizing the embodiment of the system illustrated in FIG. 1 to perform a secondary task (UAV control)
Figure 3B:
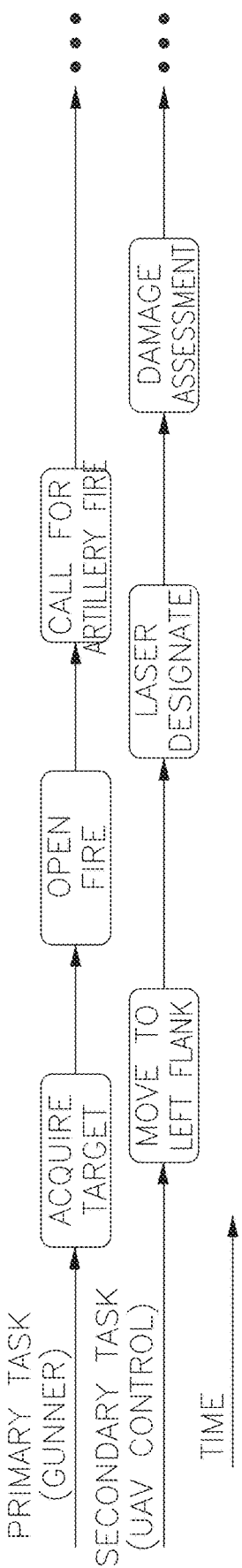
FIG. 3B is a timeline of the user of FIG. 3A switching between the primary and secondary tasks (gunner and UAV control), where the secondary task utilizes the embodiment of the system illustrated in FIG. 1.

FIG. 3A is a perspective view of a user (a soldier performing a primary task of controlling a weapon on a mobile platform (i.e., a gunner)) utilizing the embodiment of the system 100 illustrated in FIG. 1 to asynchronously perform two subtasks of a secondary task (UAV control), while the user manually performs the primary task (gunner) unassisted by the system 100. In one or more embodiments, the user can perform the primary task of acquiring targets, shooting, and calling for artillery fire all without the aid of the system 100, but the secondary task is controlled by means of the system 100. The secondary task might be divided into two subtasks, each subtask with its own message task buffer. For example, identifying a target may be done by an algorithm onboard so it would involve messages about whether or not a target has been identified, or turning on the laser designator. Additionally, in one or more embodiments, flying the UAV may involve supplying a velocity vector to the UAV and receiving status messages about fuel level or other operating status. FIG. 3B is a timeline of the user (the soldier) of FIG. 3A switching between the primary and secondary tasks (gunner and UAV control) utilizing the embodiment of the system 100 illustrated in FIG. 1. While multitasking, it is well-known that it takes time for the user to reacquire situational awareness when switching tasks. Embodiments of the present disclosure make it possible to reduce the acquisition time of the secondary task, because while the user is focused consciously on the primary task, the systems and methods of the present disclosure continue to update status messages from the secondary task, which means they are encoded and applied to the brain, bypassing the senses. Thus, the situational awareness of the secondary task is continually updated subconsiously, even as the user's senses and consciousness are involved with the primary task. The brain state decoder 101 of the system 100 is configured to decode the neural signals of the soldier and send the output signal to the command MUX 102, which sends control signals to the secondary task of operating the unmanned aerial vehicle (UAV) (e.g., moving the UAV, laser designating a target, conducting damage assessment, etc.). Additionally, a first status buffer 105 is configured to receive status information (e.g., status updates such as whether a target has been detected, or damage assessments)) from the UAV sensing task and a second status buffer 105 is configured to receive status information (e.g., status updates such as arrival at designated waypoint or low fuel indications) from the UAV movement control task. The algorithm of the status selector module 106 (e.g., Equation 1 above and depicted in FIG. 2) is configured to select the status information from one of the status buffers 105 based on a set of parameters, such as, for example, classification of the status information (e.g., an error message, a warning message, or information), the time that has elapsed since each status information message was stored in the status buffer 105, and/or the priority of the tasks to be performed utilizing the system 100. The system 100 is configured to then send the selected status information as non-sensory neural data to the user via the status MUX 107 and the brain state encoder 102. In this manner, the system 100 is configured to minimize or at least reduce the time lag (e.g., situation acquisition time) for the operator to switch between one of the gunner tasks and one of the UAV control tasks, as shown in the timeline depicted in FIG. 3B.

Figure 3C:
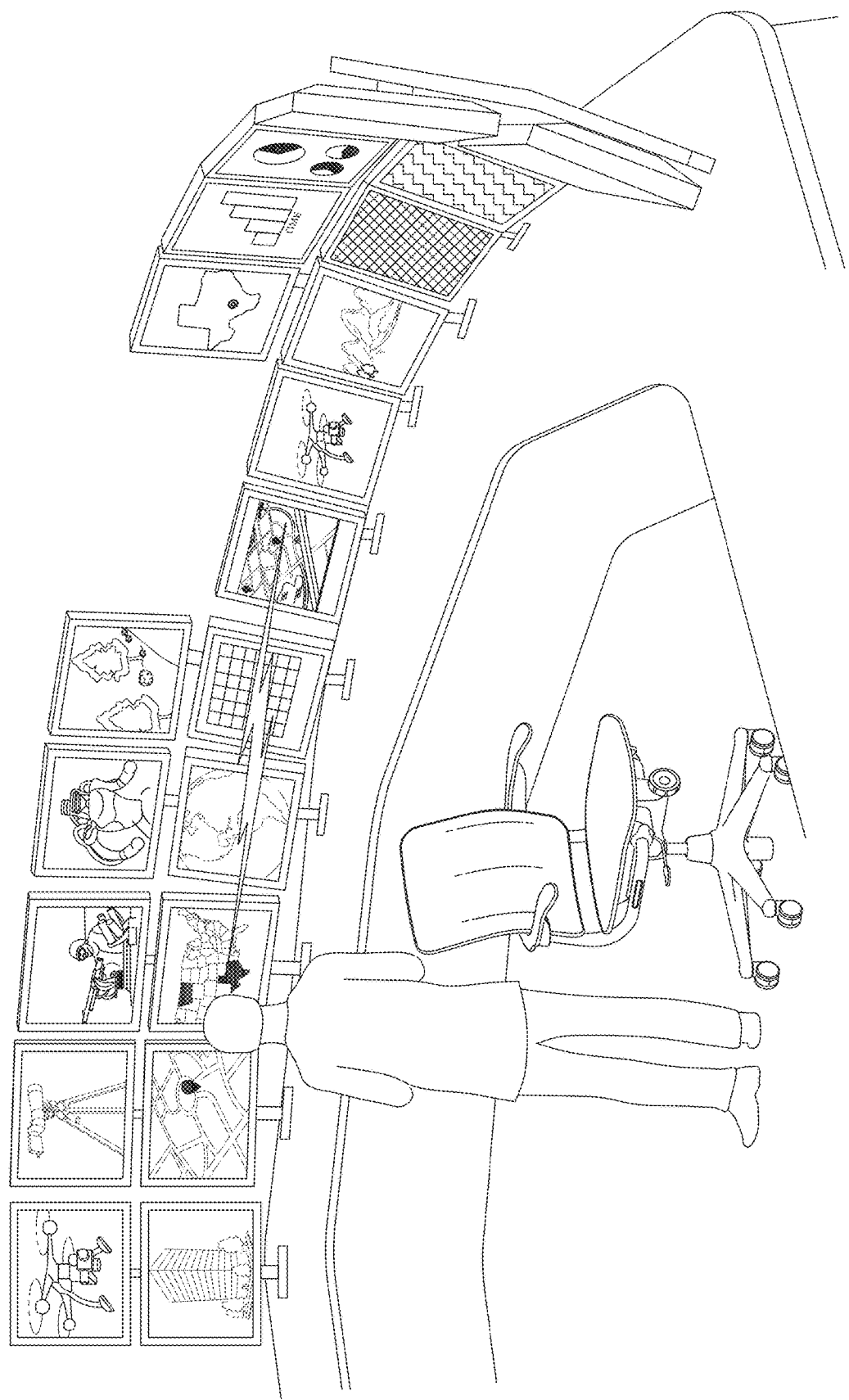
FIG. 3C is a perspective view of a user (an intelligence analyst) utilizing the embodiment of the system illustrated in FIG. 1 to asynchronously perform tasks of monitoring the content displayed on two or more computer monitors according to one embodiment of the present disclosure.

FIG. 3C is a perspective view of a user (an intelligence analyst) utilizing the embodiment of the system 100 illustrated in FIG. 1 to asynchronously perform tasks of monitoring the content displayed on two or more computer monitors according to one embodiment of the present disclosure (e.g., getting alerts when content on a monitor is urgent, and sending commands from the user to control each task controlling a monitor). The brain state decoder 101 of the system 100 is configured to decode the neural signals of the intelligence analyst and send the output signal to the command MUX 102, which sends control signals to the primary task of operating, or analyzing the information displayed on, one of the computer monitors and the secondary task of operating, or analyzing the information displayed on, another one of the computer monitors. Additionally, a first status buffer 105 is configured to receive status information (e.g., status updates such as new information appearing or alerts about particularly critical information) from one of the monitors and a second status buffer 105 is configured to receive status information (e.g., status updates) from another one of the monitors. The algorithm of the status selector module 106 (e.g., Equation 1 above and depicted in FIG. 2) is configured to select the status information from one of the status buffers 105 based on a set of parameters, such as, for example, classification of the status information (e.g., an error message, a warning message, or information), the time that has elapsed since the status information was stored in the status buffer 105, and/or the priority of the tasks to be performed utilizing the system 100. The system 100 is configured to then send the selected status information as non-sensory neural data to the user via the status MUX 107 and the brain state encoder 102. In this manner, the system 100 is configured to minimize or at least reduce the time lag for the operator to switch between operating and/or analyzing the information displayed on one of the monitors and operating and/or analyzing the information displayed on another one of the monitors. Although the system 100 has been described above as being utilized to asynchronously switch between operating and/or analyzing the information displayed on two different monitors, in one or more embodiments, the system 100 of the present disclosure may be utilized to asynchronously switch between operating and/or analyzing the information displayed on three or more different monitors.

FIG. 4 is a flowchart illustrating tasks of a method 200 of asynchronous brain control of one or more tasks according to an embodiment of the present disclosure. The one or more tasks may be one or more semi-autonomous tasks for controlling or operating a single device (e.g., a single semi-autonomous device) or the two or more tasks may be semi-autonomous tasks for controlling or operating two or more different devices (e.g., two or more different semi-autonomous devices). Additionally, the method 200 may be utilized to perform cognitive control of any semi-autonomous device capable of accepting discrete commands, such as, for instance, air vehicles (e.g., UAVs), ground vehicles, water vehicles, humanoid robots (e.g., a robot arm), or interfaces of computers.

In the illustrated embodiment, the method 200 includes a task 205 of obtaining or receiving dynamic properties of the user's brain (e.g., neural signals, blood flow, and/or electrical emanations) and decoding the neural signals of the user into control signals for controlling the two or more tasks. In one or more embodiments, the task 205 of receiving/obtaining the neural signals from the user may be performed either invasively (e.g., by electrodes surgically implanted inside the brain) or non-invasively (e.g., by electrodes placed outside the user's skull). The number of control signals decoded from the neural signals of the user in task 205 may be equal to the number of tasks performed utilizing the method 200. Additionally, in one or more embodiments, the task 205 of decoding the user's neural signals may be performed utilizing the decoder 101 described above with reference to the embodiment illustrated in FIG. 1. The control signals may be any suitable type or kind of control signals depending on the type of tasks the system is designed to control, such as, for example, steering commands to an unmanned aerial vehicle or actuation and manipulation control signals to a robot arm.

Additionally, in the illustrated embodiment, the method 200 includes a task 210 of sending the decoded neural signals as control signals to the two or more tasks (e.g., utilizing the command MUX 102 described above with reference to the embodiment illustrated in FIG. 1). The task 210 of sending the decoded neural signals as control signals to the two or more tasks may be performed by transmitting the control signals over any transmission medium suitable for the respective task (e.g., the control signals may be transmitted over a wired medium or a wireless medium).

In the illustrated embodiment, the method 200 also includes a task 215 of storing status information (e.g., status messages) obtained from each of the one or more tasks in individual status buffers (e.g., the status buffers 105 described above with reference to the embodiment illustrated in FIG. 1). The status information of the tasks may include information (e.g., general information) regarding the status of one of the tasks, a warning regarding one of the tasks, or an indication that an error occurred with one of the tasks. The number of status buffers utilized in task 215 to store the status information of the tasks is equal to the number of tasks controlled by the method 200, and each status buffer is configured to store the status information (e.g., the status updates) of only a single task. In one or more embodiments, the brain state decoder utilized in task 205 may be configured to decode the user's neural signals into any other suitable number of control signals and the task 215 may include individually storing the status information in any other suitable number of status buffers depending on the number of tasks the method 200 is configured to control. Storing the status information in individual status buffers in task 215 facilitates receiving status information asynchronously from the tasks.

In the illustrated embodiment, the method 200 also includes a task 220 of selecting the status information stored in one of the individual status buffers to send to the user. In one or more embodiments, the task 220 of selecting the status information to send to the user may be based on a set of parameters, such as, for example, a classification of the status information (e.g., an error message, a warning message, or information), the time that has elapsed since the status information was stored in the status buffer, a weighting factor on the elapsed time since storage in the status buffer, and/or the priority of the tasks to be performed utilizing the method 200. In one or more embodiments, the task 220 of selecting the status information to send to the user may be performed utilizing the embodiment of the status selector module 106 depicted in FIG. 1 and the status selector module 106 may be programmed with any suitable algorithm for prioritizing the status information, such as, for example, Equation 1 described above with reference to embodiment depicted in FIG. 2.

In the illustrated embodiment, the method 200 also includes a task 225 of sending the status information that was selected in task 220 to the user as brain stimulation montages that create a non-sensory awareness in the user of the status information (e.g., non-sensory awareness of the task state of one of the two or more tasks). That is, in one or more embodiments, the task 225 includes transmitting the selected status information of one of the tasks to the user as non-sensory neural data (e.g., the selected status information bypasses the user's senses and is transmitted directly to the user's short-term memory). In one or more embodiments, the task 225 of sending the selected status information to the user may be performed utilizing the embodiment of the status MUX 107 and the embodiment of the brain state encoder 102 described above with reference to the embodiment depicted in FIG. 1. Additionally, in one or more embodiments, the task 225 of sending the status information to the user as non-sensory neural data may be performed either invasively (e.g., by electrodes surgically implanted inside the brain) or non-invasively (e.g., by electrodes placed outside the user's skull). Sending the selected status information to the user as non-sensory neural data in task 225 (e.g., sending the selected status information directly to the user's short-term memory) reduces the amount of time it takes for the user to reacquire cognitive situational awareness of the task about which the status information was provided when switching from performing another task. Reducing the amount of time it takes the user to reacquire cognitive situational awareness enables the user to rapidly switch between performing the two or more tasks. That is, task 225, which keeps the user informed of the status of a second task via non-sensory neural data while performing a first task, minimizes or at least reduces the lag time in the user reacquiring situational awareness of the second task, which enables the user to regain effective, informed control of the second task after switching away from performing the first task. In this manner, the method 200 enables asynchronous control of the two or more tasks with low-latency, such as latency less than or equal to approximately 50 ms.

Following the task 225 of sending the selected status information to the user as non-sensory neural data, the method 200 includes a task 230 of clearing the selected status information from the status buffer in which that status information was stored.

In the illustrated embodiment, the task 205 of decoding the user's neural signals, the task 210 of sending the decoded neural signals as control signals for performing two or more tasks, the task 215 of storing status information about the two or more tasks, the task 220 of selecting status information to send to the user, the task 225 of sending the selected information to the user as non-sensory neural data, and the task 230 of clearing the selected status information from the status buffer are repeatedly performed until the operation of controlling the two or more tasks has completed. In one or more embodiments, the method 200 of the present disclosure is configured to enable continuous, asynchronous cognitive control of the two or more tasks with low-latency for a sustained duration, such as, for example, up to approximately (about) two (2) hours or more, depending on how long the encoding/decoding device can be safely interfaced to the brain of the user, and the user's fatigue level.

The above system and/or any other relevant devices or components according to embodiments of the present invention described herein may be implemented utilizing any suitable hardware, firmware (e.g. an application-specific integrated circuit), software, or a combination of software, firmware, and hardware. For example, the various components of the system may be formed on one integrated circuit (IC) chip or on separate IC chips. Further, the various components of the system may be implemented on a flexible printed circuit film, a tape carrier package (TCP), a printed circuit board (PCB), or formed on one substrate. Further, the various components of the system may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the scope of the exemplary embodiments of the present invention.

It should be understood that the drawings are not necessarily to scale and that any one or more features of an embodiment may be incorporated in addition to or in lieu of any one or more features in another embodiment. Although relative terms have been used herein to describe a spatial relationship of one element to another, it is understood that these terms are intended to encompass different orientations of the various elements and components of the invention in addition to the orientation depicted in the figures. Additionally, as used herein, the term "substantially," "about," "generally" and similar terms are used as terms of approximation and not as terms of degree, and are intended to account for the inherent deviations in measured or calculated values that would be recognized by those of ordinary skill in the art. Moreover, the tasks described above may be performed in the order described or in any other suitable sequence. Additionally, the methods described above are not limited to the tasks described. Instead, for each embodiment, one or more of the tasks described above may be absent and/or additional tasks may be performed. Furthermore, as used herein, when an element is referred to as being "on", "connected to", "coupled to", or "adjacent to" another element, it can be directly on, connected to, coupled to, or adjacent to the other element, or one or more intervening elements may be present. In contrast, when an element is referred to as being "directly on," "directly connected to", "directly coupled to", or "immediately adjacent to" another element, there are no intervening elements present.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While this invention has been described in detail with particular references to exemplary embodiments thereof, the exemplary embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, as set forth in the following claims, and equivalents thereof.

What is claimed is:

1. A closed-loop system for asynchronous brain control of at least one task, the system comprising:
    a brain state decoder configured to decode neural signals of a user into control signals for controlling the at least one task;
    a task interface module configured to transmit the control signals to the at least one task, store status information comprising a plurality of messages regarding each of the at least one task, and select one message of the plurality of messages to transmit to the user; and
    a brain state encoder configured to map the one message received from the task interface module into brain state montages for transmission to the user.

2. The system of claim 1, wherein the task interface module comprises:
    at least one status buffer configured to store the status information of the at least one task; and
    a status selector module programmed with an algorithm configured to select the one message from the plurality of messages regarding the at least one task based on a classification of the status information, a recency parameter, and a priority of the at least one task.

3. The system of claim 2, wherein the algorithm further comprises a weighting parameter weighing on the recency parameter.

4. The system of claim 3, wherein the weighting parameter is a constant value.

5. The system of claim 3, wherein the weighting parameter is a function of the recency parameter.

6. The system of claim 5, wherein the function is a non-linear function.

7. The system of claim 2, wherein the algorithm is:

$$\text{BufferPriorities}=P_{buffer}*(\max_{msg_1}{}^{msg_n}(\text{UrgencyValue}_{msg}*R*\Delta t_{msg}))$$

wherein $msg_1$ through $msg_n$ are the plurality of messages regarding the at least one task, $P_{buffer}$ is an apriori value representing a priority of each of the at least one status buffer, $\text{UrgencyValue}_{msg}$ is an urgency value based on a classification of each of the plurality of messages, $\Delta t_{msg}$ is a recency parameter reflecting a recency of the plurality of messages, and R is a weighting parameter reflecting an importance of the recency parameter, and wherein the one message selected by the status selector module is a message of the plurality of messages having a highest BufferPriorities value.

8. The system of claim 2, wherein the task interface module further comprises a command multiplexer configured to transmit the control signals to the at least one task.

9. The system of claim 2, wherein the task interface module further comprises a status multiplexer configured to transmit the status information of the one of the at least one task to the brain state encoder.

10. The system of claim 1, wherein the at least one task is performed on a same semi-autonomous device or on two or more separate semi-autonomous devices.

11. A method for asynchronous control of at least one task in a closed-loop system, the method comprising:
    decoding, with a brain state decoder, neural signals of a user into a command signal;
    transmitting the command signal to the at least one task;
    storing, in at least one status buffer, status information comprising a plurality of messages regarding each of the at least one task;
    selecting, with a status selector module programmed with an algorithm, one message of the plurality of messages; and
    encoding, with a brain state encoder, the one message into brain state montages for transmission to the user.

12. The method of claim 11, further comprising obtaining the neural signals invasively or non-invasively from the user.

13. The method of claim 11, further comprising transmitting the brain state montages directly to the user's short-term memory, and wherein the brain state montages are configured to create a non-sensory cognitive perception in the user of the status information regarding the at least one task.

14. The method of claim 11, wherein the algorithm comprises a classification of the plurality of messages, a recency parameter, and a priority of the plurality of messages.

15. The method of claim 14, wherein the algorithm further comprises a weighting parameter weighing on the recency parameter.

16. The method of claim 15, wherein the weighting parameter is a constant value.

17. The method of claim 15, wherein the weighting parameter is a function of the recency parameter.

18. The method of claim 17, wherein the function is a non-linear function.

19. The method of claim 11, wherein the algorithm is:

$$\text{BufferPriorities}=P_{buffer}*(\max_{msg_1}{}^{msg_n}(\text{UrgencyValue}_{msg}*R*\Delta t_{msg})),$$

wherein $msg_1$ through $msg_n$ are the plurality of messages regarding the at least one task, $P_{buffer}$ is an apriori value representing a priority of each of the at least one status buffer, $\text{UrgencyValue}_{msg}$ is an urgency value based on a classification of each of the plurality of messages, $\Delta t_{msg}$ is a recency parameter reflecting a recency of the plurality of messages, and R is a weighting parameter reflecting an importance of the recency parameter, and wherein the one message selected by the status selector module is a message of the plurality of messages having a highest BufferPriorities value.

20. A closed-loop system for asynchronous brain control of at least two tasks, the system comprising:
    means for decoding neural signals of a user into a command signal;
    means for transmitting the command signal to at least one task;
    means for storing status information comprising a plurality of messages regarding each of the at least one task;
    means for selecting one message of the plurality of messages regarding the at least one task; and
    means for encoding the one message regarding the at least one task into brain state montages for transmission to the user.

* * * * *